United States Patent
Ingraham

(10) Patent No.: US 11,992,502 B2
(45) Date of Patent: May 28, 2024

(54) ANIMAL TREATMENT PASTES AND OINTMENTS AND METHODS OF USING SAME

(71) Applicant: Challen Ingraham, Tabernacle, NJ (US)

(72) Inventor: Challen Ingraham, Tabernacle, NJ (US)

( * ) Notice: Subject to any disclaimer, the term of this patent is extended or adjusted under 35 U.S.C. 154(b) by 367 days.

(21) Appl. No.: 17/503,583

(22) Filed: Oct. 18, 2021

(65) Prior Publication Data

US 2023/0119840 A1  Apr. 20, 2023

(51) Int. Cl.
| | | |
|---|---|---|
| *A61K 33/00* | (2006.01) |
| *A61K 31/4015* | (2006.01) |
| *A61K 33/30* | (2006.01) |
| *A61K 33/34* | (2006.01) |
| *A61K 35/644* | (2015.01) |
| *A61K 47/24* | (2006.01) |
| *A61K 47/36* | (2006.01) |
| *A61K 47/46* | (2006.01) |

(52) U.S. Cl.
CPC .......... *A61K 33/34* (2013.01); *A61K 31/4015* (2013.01); *A61K 33/30* (2013.01); *A61K 35/644* (2013.01); *A61K 47/24* (2013.01); *A61K 47/36* (2013.01); *A61K 47/46* (2013.01)

(58) Field of Classification Search
CPC ...................................................... A61K 33/00
See application file for complete search history.

(56) References Cited

FOREIGN PATENT DOCUMENTS

WO   WO-2019173213 A1 *  9/2019  ............. A61K 31/19

* cited by examiner

*Primary Examiner* — Rosanne Kosson
(74) *Attorney, Agent, or Firm* — SLEMAN & LUND LLP

(57) ABSTRACT

A treatment paste includes copper sulfate, zinc oxide powder, an emulsifier, a stabilizer, pine tar, and an antiseptic solution.

9 Claims, No Drawings

ANIMAL TREATMENT PASTES AND OINTMENTS AND METHODS OF USING SAME

FIELD OF THE DISCLOSURE

The present disclosure relates to antimicrobial ointments and pastes for treating certain diseases in animals. More particularly the present disclosure relates to ointments and pastes for hoofed animals having conditions, such as laminitis.

BACKGROUND OF THE DISCLOSURE

Hoof thrush in horses and other hoofed animals has been treated mostly with liquid treatments. Thrush is a very common bacterial and/or fungal infection that occurs on the hoof of a horse or similar animal. Chlorhexidine ointments in a hydrophilic base are well-known for topically treating surface wounds in animals.

White line disease, or WLD, is characterized by an invasion of bacteria and fungi that destroy hoof-wall tissue. A crack or separation in the hoof wall, which can be caused by mechanical factors such as long toes or a club foot, may create such an opportunity for infection.

SUMMARY OF THE DISCLOSURE

In some embodiments, a treatment paste includes copper sulfate, zinc oxide powder, an emulsifier, a stabilizer pine tar, and an antiseptic solution.

DETAILED DESCRIPTION

The present disclosure describes compositions for treating horses or similar animals. In one embodiment, certain. Ingredients as presented in Table 1 below are used to make a first "max-dose" formula, their ratios being provided as exemplary, but non-limiting:

TABLE 1

| Component | Quantity |
| --- | --- |
| Copper sulfate | ¼ cup |
| Zinc oxide powder | 4 tablespoons |
| Lecithin (emulsifier) | 2 teaspoons |
| Guar gum (stabilizer) | ½ teaspoon |
| Pine tar | 2 tablespoons |
| Honey | ½ cup |
| Betadine ® | 2 tablespoon |

It will be understood that some of the ingredients may be optional, and that that quantity of each ingredient may be varied. In at least some examples, the method of making the composition includes mixing the zinc oxide powder, Betadine® and lecithin in the quantities shown. After sufficient mixing, the honey, copper sulfate and guar gum may be added. Mixing the ingredients may occur at room temperature and may continue until the composition changes color from green to brown to produce the finished gel-like product. The product may be packaged for sale in a squeezable tube or small container.

In another embodiment, certain ingredients are used as presented in Table 2 below to make a second formula, their ratios being provided as exemplary, but non-limiting:

TABLE 2

| Component | Quantity |
| --- | --- |
| Copper sulfate | 2 teaspoons |
| Zinc oxide powder | 4 tablespoons |
| Lecithin (emulsifier) | 2 teaspoons |
| Guar gum (stabilizer) | ½ teaspoon |
| Pine tar | 2 tablespoons |
| Honey | ½ cup |
| Betadine ® | 2 tablespoons |

In yet another embodiment, certain ingredients are used as presented in Tables 3 or 5 below to make additional formulas, their ratios being provided as exemplary, but non-limiting:

TABLE 3

| Component | Quantity |
| --- | --- |
| Copper sulfate | ¼ cup |
| Zinc oxide powder | ¼ cup |
| Lecithin (emulsifier) | 2 teaspoons |
| Guar gum (stabilizer) | 1 teaspoon |
| Pine tar | ¼ cup |
| Honey | ½ cup |

TABLE 4

| Component | Quantity |
| --- | --- |
| Copper sulfate | 2 teaspoons |
| Zinc oxide powder | ¼ cup |
| Lecithin (emulsifier) | 2 teaspoons |
| Guar gum (stabilizer) | 1 teaspoon |
| Pine tar | ¼ cup |
| Honey | ½ honey |

It will be understood that some of the ingredients may be optional, and that that quantity of each ingredient may be varied. In at least some examples, the method of making the composition includes mixing the zinc oxide powder, Betadine® and lecithin in the quantities shown. After sufficient mixing, the honey, copper sulfate and guar gum may be added. In this example, substantially less copper sulfate is used than in the first "max-dose" formula. Mixing the ingredients may occur at room temperature and may continue until the composition changes color from green to brown to produce the finished gel-like product. In some examples, after mixing, the ingredients may be heated to 180° then stirred until the composition cools down. In some examples, approximately 5 minutes of heating causes an exothermic reaction with the zinc and copper sulfate that results in a chemical change which creates zinc sulfate. The product may be packaged for sale in a squeezable tube or small container.

In some examples, the composition may be applied as a preventative measure. In some examples, the composition is applied every other day for two weeks. Alternatively, the composition may be applied regularly with no currently known side effects.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A treatment paste composition comprising therapeutically effective amounts of:
   (a) copper sulfate;
   (b) zinc oxide powder;
   (c) an emulsifier;
   (d) a stabilizer; and
   (e) an antiseptic solution.

2. The treatment paste of claim 1, wherein the emulsifier comprises lecithin.

3. The treatment paste of claim 1, wherein the stabilizer comprises guar gum.

4. The treatment paste of claim 1, wherein the stabilizer comprises a vegetable-based stabilizer.

5. The treatment paste of claim 1, wherein the antiseptic solution comprises povidone-iodine.

6. The treatment past of claim 1, further comprising honey.

7. A treatment paste consisting of copper sulfate, zinc oxide powder, an emulsifier, a stabilizer, pine tar and an antiseptic solution.

8. A treatment paste composition comprising therapeutically effective amounts of:
   (a) copper sulfate; (b) zinc oxide powder; (c) lecithin; (d) guar gum; (e) honey; and
   (f) an antiseptic solution.

9. A method of making the treatment paste composition of claim 8, comprising:
   (i) mixing the zinc oxide powder, the antiseptic solution and the lecithin; and
   (ii) adding to the mixture of step (i) the honey, the copper sulfate and the guar gum.

\* \* \* \* \*